(12) United States Patent
Shvartsburg et al.

(10) Patent No.: US 7,491,930 B2
(45) Date of Patent: Feb. 17, 2009

(54) HOOKED DIFFERENTIAL MOBILITY SPECTROMETRY APPARATUS AND METHOD THEREFORE

(75) Inventors: Alexandre A. Shvartsburg, Richland, WA (US); Keqi Tang, Richland, WA (US); Yehia M. Ibrahim, Richland, WA (US); Richard D. Smith, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 248 days.

(21) Appl. No.: 11/617,889

(22) Filed: Dec. 29, 2006

(65) Prior Publication Data

US 2008/0156978 A1 Jul. 3, 2008

(51) Int. Cl.
*H01J 49/06* (2006.01)
*H01J 49/26* (2006.01)
*B01D 59/44* (2006.01)

(52) U.S. Cl. .................. 250/287; 250/281; 250/282; 250/286; 250/288; 250/293; 250/396 R (58) Field of Classification Search ................ 250/281, 250/282, 286, 287, 288, 293, 396 R
See application file for complete search history.

(56) References Cited

U.S. PATENT DOCUMENTS 7,339,166 B2 *   3/2008   Tang et al. ................. 250/288
7,397,027 B2 *   7/2008   Li ............................ 250/287

OTHER PUBLICATIONS

Shvartsburg, et al., Anal. Chem 2006, 78, pp. 3706-3714.
Shvartsburg, et al., FAIMS Analyzers: Evaluation of Planar and Hooked Geometries, 2007 presentation.
Shvartsburg, et al, J. Am. Soc for Mass Spectrom, 2004, 15, pp. 1487-1498.
Guevremont, et al., Rev. Sci. Instrum, 70, 2, Feb. 1999, pp. 1370-1383.
Guevremont, et al, J. Am. Soc. Mass Spectrom., 2001, 12, pp. 1320-1330.
Guevremont, et al, J. Am. Soc. Mass Spectrom., 2005, 16, pp. 349-362.
Shvartsburg, et al., J. Am. Soc for Mass Spectrom., 2005, 12, pp. 2-12.

* cited by examiner

*Primary Examiner*—Nikita Wells
(74) *Attorney, Agent, or Firm*—James D. Matheson (57) ABSTRACT

Disclosed are a device and method for improved interfacing of differential mobility spectrometry (DMS) or field asymmetric waveform ion mobility spectrometry (FAIMS) analyzers of substantially planar geometry to subsequent or preceding instrument stages. Interfacing is achieved using curved DMS elements, where a thick ion beam emitted by planar DMS analyzers or injected into them for ion filtering is compressed to the gap median by DMS ion focusing effect in a spatially inhomogeneous electric field. Resulting thinner beams are more effectively transmitted through necessarily constrained conductance limit apertures to subsequent instrument stages operated at a pressure lower than DMS, and/or more effectively injected into planar DMS analyzers. The technology is synergetic with slit apertures, slit aperture/ion funnels, and high-pressure ion funnel interfaces known in the art which allow for increasing cross-sectional area of MS inlets. The invention may be used in integrated analytical platforms, including, e.g., DMS/MS, LC/DMS/MS, and DMS/IMS/MS that could replace and/or enhance current LC/MS methods, e.g., for proteomics research.

43 Claims, 9 Drawing Sheets

Fig. 8c ated by the U.S.
HOOKED DIFFERENTIAL MOBILITY SPECTROMETRY APPARATUS AND METHOD THEREFORE This invention was made with Government support under Contract DE-AC06-76RLO1830 awarded by the U.S. Department of Energy. The Government has certain rights in the invention.

FIELD OF THE INVENTION

The invention is in the field of ion mobility spectrometry (IMS) and mass spectrometry. More specifically, it is an apparatus and method for improved interfacing between differential mobility spectrometry (DMS) or field asymmetric waveform ion mobility spectrometry (FAIMS) analyzers and various stages of analytical instrumentation.

BACKGROUND OF THE INVENTION

Mass spectrometry (MS) is the core technology of state-of-the-art biological analyses, including proteomics, metabolomics, and other "omic" fields of the post-genomic era. However, even with the formidable power of modern MS, nearly all real-world samples require prior separations. Those separations had traditionally been performed in the condensed phase (liquid or solid), e.g., liquid chromatography (LC), capillary electrophoresis (CE), capillary isoelectric focusing (CIEF), and gel electrophoresis in one or two dimensions such as sodium dodecyl sulfate polyacrylamide gel electrophoresis (SDS-PAGE) and 2-D gel. A major attraction of separations based on ion transport, including differential mobility spectrometry (DMS), is a huge throughput gain over condensed-phase methods allowed by high speed of ion motion in gases compared to that in liquids.

DMS, also termed field asymmetric waveform ion mobility spectrometry (FAIMS), or ion mobility increment spectrometry, has emerged as a powerful analytical tool of broad utility for separation of ionic mixtures and characterization of ions in the gas phase, especially in conjunction with mass spectrometry (MS). DMS analyses are based on the difference between ion mobilities at high and low electric fields. Ions are filtered while pulled through a gap between two electrodes carrying an asymmetric waveform by gas flow or, longitudinal electric field. The spatial form of electric field inside the gap that controls DMS performance depends on the gap shape, and several geometries including planar, cylindrical, and spherical have been considered. Recent work has established that the highest resolution and best resolution-sensitivity trade-off are provided by homogeneous electric field found in planar DMS devices.

Instruments that combine DMS with MS offer exceptional sensitivity, specificity, and dynamic range. The applications of DMS/MS span the fields such as pharma R&D, toxicology, proteomics, metabolomics, health care, natural resource management, product quality assurance, and environmental monitoring. The advent of LC/DMS/MS and DMS/IMS/MS platforms has made DMS particularly attractive for analyses of extremely complex samples ubiquitous in proteomics and metabolomics.

Despite significant advantages of planar DMS over curved geometries in terms of resolution, duty cycle, and quantification accuracy/dynamic range, all commercial DMS/MS systems to date have employed cylindrical DMS designs comprising two coaxial electrodes, where ions are focused to the annular gap median by inhomogeneous electric field. One reason for this has been that cylindrical DMS (in the configuration with gas flow along the axis, implemented, e.g., in the Ionalytics Selectra®) is particularly easy to couple to MS using a hemispherical terminus. In the homogeneous electric field of planar DMS, ions are free to spread both across and laterally to the gap under the influence of diffusion and mutual Coulomb repulsion. This eventually produces ribbon-shaped ion beams with the cross-section approximately defined by the DMS gap. Such wide beams cannot be transmitted through standard MS inlets (of either the capillary or orifice/curtain plate type) without great ion losses.

Slit apertures known in the art provide a greater overlap with ribbon-shaped ion beams emitted by planar DMS than circular apertures, reducing ion losses at the interfaces of planar DMS with MS, IMS, or other subsequent stages and thus improving analytical sensitivity. Ions captured by such apertures may be effectively focused using electrodynamic ion funnels taught, e.g., in U.S. Pat. Nos. 6,979,816, 6,818,890, and 6,967,325, incorporated herein. High-pressure ion funnels allow expanding the area of slit apertures, which further increases the utilization of ions delivered by DMS. Nonetheless, the slit is still much smaller than the opening of DMS gap at any reasonable pressure and pumping capacity in the front MS region, and substantial ion losses remain.

Hence one would desire to focus thick ribbon-like ion beams generated by planar DMS prior to the conductance limit to following instrument stages, including, e.g., MS, IMS, and like stages operated at lower gas pressure. Achieving that objective requires new devices and methods.

In another aspect, ions may initially be injected into DMS at various points across the gap, including some close to electrodes. In cylindrical DMS, those ions are rapidly bunched near the gap median by focusing due to inhomogeneous electric field, which minimizes non-selective ion loss to the electrodes immediately upon injection. In contrast, in planar DMS ions injected proximately to electrodes are commonly lost because of diffusion and Coulomb repulsion, which may contribute to a lower sensitivity of prior planar DMS systems compared to cylindrical DMS. Hence it may be advantageous to bunch ions injected into planar DMS to the gap median prior to their separation.

SUMMARY OF THE INVENTION

Disclosed herein is an apparatus and method for focusing rectangular ion beams output by planar DMS analyzers into thinner beams that could be more effectively transmitted to subsequent instrument stages through constrained apertures. Those stages include, but are not limited to, mass spectrometry (MS), ion mobility spectrometry (IMS), and combinations, including, e.g., IMS/MS. Examples of integrated systems thus include, e.g., DMS/MS, DMS/IMS, LC/DMS/MS, LC/DMS/IMS, DMS/IMS/MS, and LC/DMS/IMS/MS.

According to the invention, a substantially planar DMS analyzer is interfaced to a subsequent or preceding stage using a curved DMS element, where a thick ion beam emitted by said analyzer or injected into it for ion filtering is compressed to the gap median by a DMS ion focusing effect in a spatially inhomogeneous electric field. To minimize ion losses in the curved element, the range of DMS separation parameters selected by the periodic asymmetric waveform $U_D(t)$ and dc compensation voltage (CV) applied must substantially include the range set by operation of said DMS analyzer. Because of ion focusing in curved geometries, the CV transmission window is always broader for curved than for planar DMS. Hence, in one aspect of the invention, focusing of ions after their separation by a substantially planar DMS analyzer neither affects its high resolution nor causes significant ion losses. However, thinner ion beams created by such focusing are more completely transmitted to subsequent instrument stages through constrained apertures. In another aspect of the invention, ion focusing compresses ion beams upon their injection into DMS, which may reduce non-selective loss of ions injected near electrodes due to diffusion and Coulomb repulsion. As always with curved DMS geometries, strength of ion focusing and thus resulting sensitivity gain tends to increase at higher absolute CV.

As all asymmetric $U_D(t)$ profiles induce ion focusing in curved DMS, various profiles may be used in the apparatus of invention and the substantially planar DMS coupled thereto or integrated therewith. In particular, rectangular, bisinusoidal, clipped-sinusoidal, and other waveforms known in the art of FAIMS may be employed, without limitation. Waveforms effecting higher-order differential ion mobility spectrometry (HODIMS), where ions are separated primarily by the third (i.e., the $4^{th}$ power) or higher terms of the polynomial representing the expansion of ion mobility as a function of electric field, may also be used.

As in DMS systems known in the art, ions may be carried through the apparatus of invention by gas flow, in particular an extension of the flow through the DMS analyzer coupled thereto. Alternatively, ions may be driven through said apparatus by a relatively weak dc component of electric field directed along the gap at each point. Such a field may be created by segmenting curved electrodes of the apparatus longitudinally and applying a ladder of dc voltages to the segments. In an embodiment, those dc voltages and $U_D(t)$ could be co-applied to electrodes using an electronic scheme including capacitors and resistances known in the art, similar to that implemented with ion funnels. The gas flow and longitudinal electric field could be combined in the same device.

One may desire to couple multiple DMS analyzers to one subsequent instrument stage, e.g., to overcome the charge capacity limitations of a single analyzer or to improve the ionization efficiency and thus analytical sensitivity using multiple ion sources (for example, in ESI), but is not limited thereto. Hence, in an embodiment, one set of curved electrodes receives ions from two or more substantially planar DMS analyzers.

It may be advantageous to deliver ions from one ion source or instrument stage to multiple DMS analyzers, e.g., to overcome the charge capacity limitation of a single analyzer, but is not limited thereto. Hence, in another embodiment, one set of curved electrodes delivers ions to two or more substantially planar DMS analyzers.

It is desirable to reduce loss of ions both after injection into DMS and during transmission from DMS to subsequent stages. In an embodiment, the system features two curved electrode sets, one delivering ions to and the other receiving ions from one or more substantially planar DMS analyzers. In particular, two DMS analyzers could be involved.

DMS separation parameters in the apparatus of invention and the DMS analyzer could be matched using different gap widths (g) and proportional $U_D(t)$ amplitudes (known as dispersion voltage, DV). However, the same (g) and $U_D(t)$ would simplify the instrument design and operation. In an exemplary embodiment, gaps between curved electrodes and between DMS analyzer electrodes have equal width and coincident median at the point of closest mutual proximity, and the same waveform is applied to said curved electrodes and to said DMS analyzer electrodes.

The apparatus of invention and a substantially planar DMS analyzer could be coupled or integrated more easily or precisely if one or more of the curved electrodes are contiguous with one or more electrodes of the DMS analyzer. In an exemplary embodiment, one curved electrode is contiguous with one planar DMS electrode and the other curved electrode is contiguous with the other planar DMS electrode such that $U_D(t)$ is loaded simultaneously on said curved electrodes and DMS analyzer electrodes coupled thereto or integrated therewith.

While the invention could use various curved electrode shapes, perhaps the easiest to manufacture are cylinders having cylindrical geometries where DMS ion focusing is best characterized. Hence, in an exemplary embodiment, the curved electrodes are cylindrical segments produced by resection of an angular arc from two coaxial cylinders and positioned such that the cylindrical axis is parallel to the DMS analyzer plane.

While the angular span of cylindrical parts may vary in the range of from 0 to about 270°, and more particularly from about 30° to about 180°, a value of ~90° in the exemplary embodiment is convenient for design and allows inserting a planar DMS into an MS system without changing orientation of the ion source or other preceding instrument stage.

In the configuration of the exemplary embodiment, the focusing field strengthens with increasing cylindrical curvature, but the ion path length through it, and thus the ion residence time in the focusing element, decrease: in the limits of zero and infinite curvature, no focusing will occur. Therefore, there must be a finite curvature providing maximum focusing effect, with the optimum depending on ion properties and experimental conditions.

The cylindrical curvature may be expressed in terms of the radius of annular gap median. The preferred radii would be between about 1 mm and about 100 mm, and more particularly between about 3 mm and about 30 mm. The value of (g) between curved electrodes would preferably be set equal to that in the DMS analyzer described above, but otherwise could be chosen to maximize ion transmission within realistic engineering constraints. Preferred values for atmospheric pressure operation would range between about 0.2 mm and about 10 mm, and more particularly between about 0.4 mm and about 5 mm.

Operation of DMS analyzers at reduced gas pressure is known in the art to increase resolution, because lower gas number density allows higher normalized electric field without electrical breakdown. The apparatus of invention may use gas at other than atmospheric pressure ($P_0$) to interface DMS analyzers operated at such other pressure ($P_{OP}$). In that case, preferred ranges for gap width stated above could be scaled by $P_0/P_{OP}$. In particular, optimum gaps for reduced-pressure operation would be wider than those selected for operation at 1 atm.

DETAILED DESCRIPTION

Described herein is a DMS apparatus of a new "hooked" design, comprising shaped segments including, but not limited to, planar and cylindrical, where ions separated in the first DMS region are subsequently focused in the second DMS region using inhomogeneous electric field. A voltage applied to a pair of curved electrodes creates a spatially inhomogeneous electric field in the gap therebetween. As known in the art, when the voltage is periodic and asymmetric, the electric field forces ions of the type set by $U_D(t)$ polarity to bunch near the gap median. That effect is used to focus ions in cylindrical DMS and its hemispherical terminus, but DMS resolution is impaired and planar DMS provides the highest resolution (see, e.g., *Anal. Chem.* 2006, 78, 3706). In the method and apparatus of the invention, focusing occurs after DMS separation and hence does not affect resolution. Compression of the ion beam to the gap median improves transmission through the slit-shaped inlet of subsequent ion stages, e.g., MS, IMS, or IMS/MS. The resulting sensitivity gain has been benchmarked by measurements for representative analytes vs. an otherwise identical planar DMS system. The evaluation is extended to several aperture sizes reflecting a range of possible MS inlet conditions. Applications envisioned here include, e.g., enabling practical high-resolution DMS analyses via coupling of planar DMS devices to MS or IMS/MS stages, particularly, but not exclusively, in conjunction with slit aperture and/or ion funnel interfaces described herein.

Figure 1:
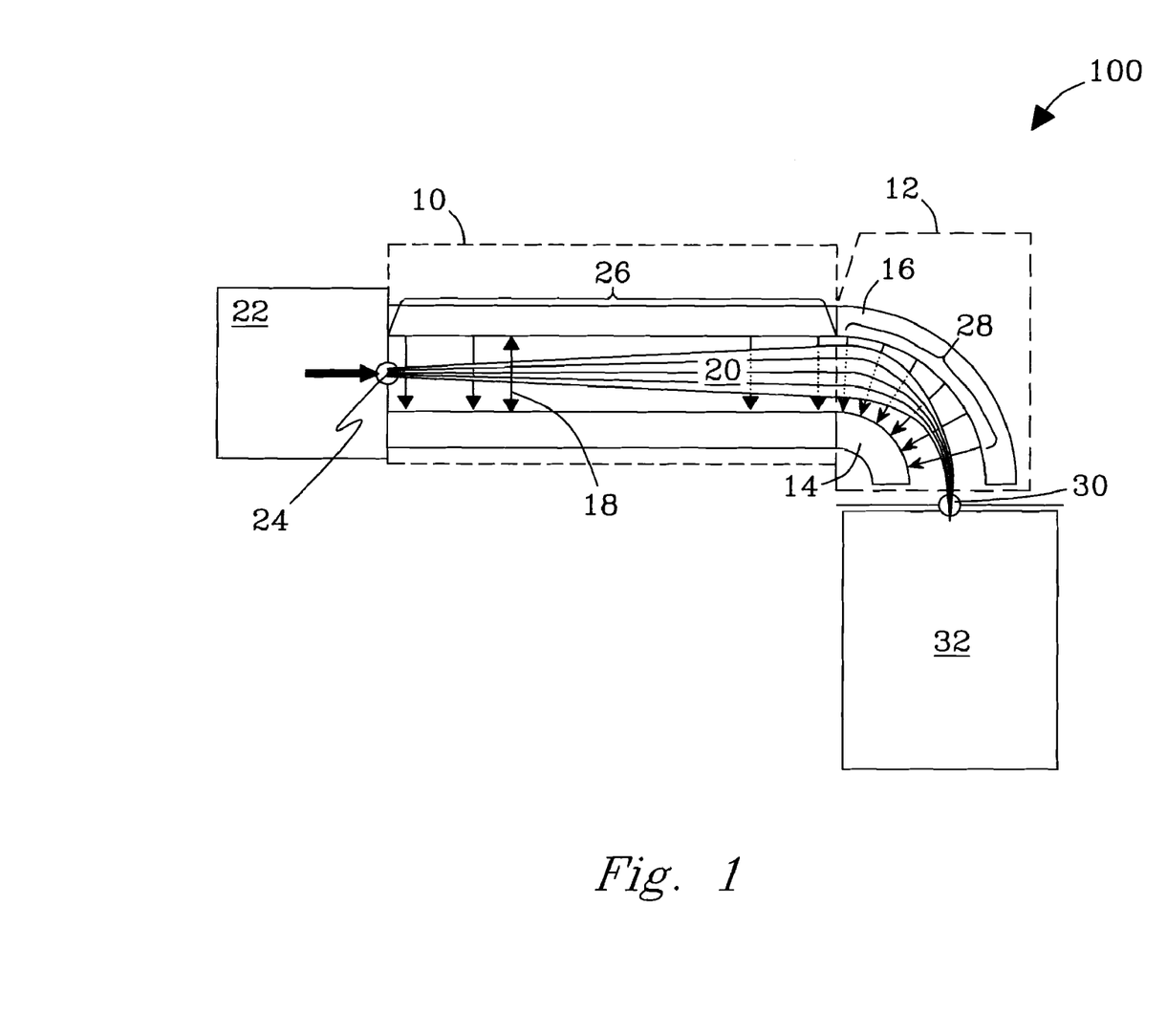
FIG. 1 is a cross-sectional view of a "hooked" DMS apparatus, according to one embodiment of the invention.

FIG. 1 illustrates a cross-section of a DMS apparatus 100 of a "hooked" design, according to one embodiment of the invention. Apparatus 100 is a planar DMS analyzer with improved interface to subsequent stages, including, but not limited to, MS, IMS, and IMS/MS stages of various types. In the figure, apparatus 100 includes a substantially planar DMS analyzer 10, integrated with a "hooked" DMS element 12 comprising two curved electrodes, 14 and 16, with a gap 18 therebetween that receives an ion beam 20 from DMS analyzer 10, to which ions are injected from an ion source or preceding instrument stage 22 via ion aperture 24. Width of gap 18 is selected in the range of from about 0.2 mm to about 10 mm, and, more particularly, from about 0.4 mm to about 5 mm. The radius of annular gap median is selected in the range from about 1 mm to about 100 mm, and more particularly from about 3 mm to about 30 mm. Gap 18 is filled with a suitable gas as will be practiced by those of skill in the art.

As usual, DMS separation is provided by a uniform electric field 26 in planar analyzer 10. Electrode 14 carries the $U_D(t)$ and electrode 16 carries the CV that jointly establish inhomogeneous electric field 28 over gap 18, which focuses ion beam 20 received from DMS analyzer 10 toward the gap median. Beam 20 is thus compressed, becoming thinner compared to diffuse beam 20 received from analyzer 10. Thus, ion beam 20 exiting apparatus 100 is more effectively transmitted via aperture 30 to subsequent stage 32, e.g., an MS or IMS. In the instant embodiment, curved electrodes 14 and 16 are cylindrical segments produced by resection of an angular arc from two coaxial cylinders and positioned such that the cylindrical axis is parallel to the plane of analyzer 10. The median of gap 18 is substantially coincident with the median of the gap between planar electrodes of analyzer 10 at the point of closest proximity between curved electrodes 14 and 16 and electrodes of analyzer 10. In the instant embodiment, apparatus 100 focuses ion beam 20 over the angular span of 90 degrees as measured from the drift vector in DMS analyzer 10, but is not limited. In other embodiments, curved electrodes 14 and 16 may provide an angular span of from about 0 degrees to about 270 degrees and more particularly from about 30 degrees to about 180 degrees. No limitations are thus intended.

Ionization sources suitable for use in conjunction with the invention include, but are not limited to, electrospray (ESI), thermospray, sonic spray, desorption ESI (DESI), matrix-assisted laser desorption ionization (MALDI) and atmospheric pressure MALDI (AP-MALDI), surface-enhanced laser desorption ionization (SELDI), chemical ionization (CI) and atmospheric pressure CI (APCI), photoionization and atmospheric pressure photoionization (APPI), laser vaporization or desorption, secondary ion ionization, arc discharge, inductively coupled plasma (ICP), coronary or cathode discharge, electron impact (EI), liquid evaporation, liquid clustering, "pick-up", and combinations thereof.

The invention may also be used to interface DMS analyzers operating on principles other than FAIMS, including, but not limited to, ion mobility spectrometers with alignment of the dipole direction (IMS-ADD) and higher-order differential ion mobility spectrometers (HODIMS). The invention may be used with MS systems including, e.g., quadrupole, quadrupole ion trap, Orbitrap, Fourier transform ion cyclotron resonance (FTICR), time-of-flight (TOF), magnetic sector, and combinations thereof without limitation.

Asymmetric waveforms for focusing ions include, e.g., clipped-sinusoidal, bisinusoidal, square, and their derivatives and superpositions. The exemplary embodiment employs a bisinusoidal $U_D(t)$ described by Shvartsburg et al. (Anal. Chem. 2006, 78, 3706) incorporated herein, but is not limited thereto. In the exemplary embodiment, the $U_D(t)$ with frequency of $w_c$=750 kHz is produced by a power supply that adds 750 kHz and 1500 kHz harmonics (with 2:1 amplitude ratio) output by a standard resonating LC circuit known in the art.

Figure 2:
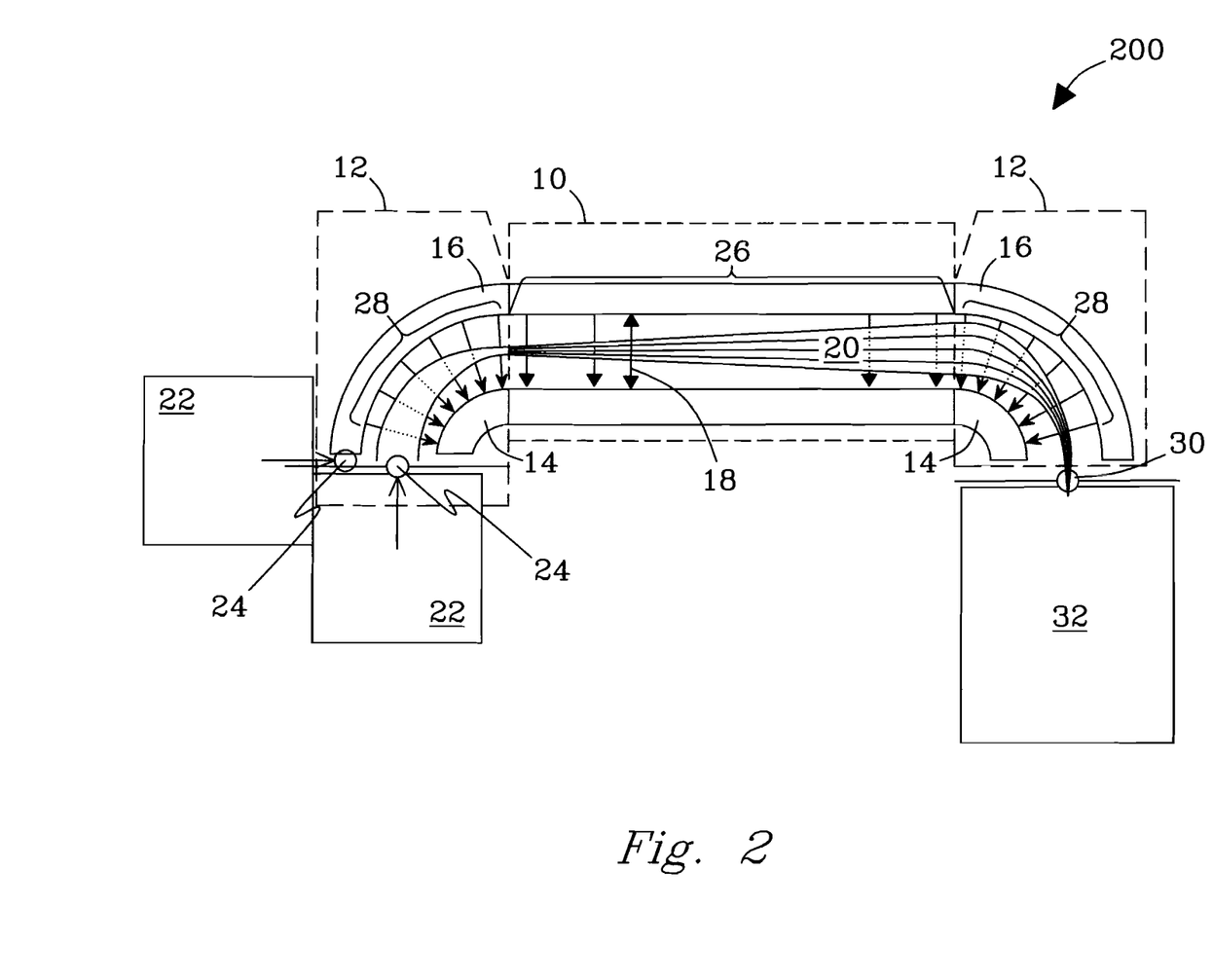
FIG. 2 is a cross-sectional view of a "hooked" DMS apparatus, according to another embodiment of the invention.

FIG. 2 illustrates a cross-section of a "hooked" DMS apparatus 200, according to another embodiment of the invention. In the instant embodiment, apparatus 200 includes a planar DMS analyzer 10 integrated with two "hooked" elements 12, each comprising two curved electrodes 14 and 16 with gap 18 therebetween. The first "hooked" element 12 receives ion beam 20 from an ion source or preceding stage 22 through aperture 24. As shown in FIG. 2, position of ion source or preceding stage 22 is not limited and, in particular, may be orthogonal or inline with ion beam 20. The second "hooked" DMS element 12, receiving ions from DMS analyzer 10, is in front of subsequent stage 32, e.g., an MS or IMS. Analyzer 10 filters ions using a uniform electric field 26. Electrode 14 carries $U_D(t)$ and electrode 16 carries the CV that jointly establish inhomogeneous electric field 28 over gap 18 which focuses ion beam 20 introduced thereto toward the gap median. Thus, beam 20 is compressed, becoming thinner compared to diffuse beam 20 received from preceding stage 22 (for first element 12) or DMS analyzer 10 (for second element 12). Ion beam 20 entering apparatus 200 is more effectively injected into DMS analyzer 10 and the beam exiting apparatus 200 is more effectively transmitted via aperture 30 to subsequent stage 32. In the instant embodiment, each stage 12 provides an angular turn of about 90° as measured from the drift vector in DMS analyzer 10 to which each element 12 is coupled or integrated, but is not limited.

In other embodiments, curved electrodes 14 and 16 receive ions from two planar DMS analyzers 10. In yet other embodiments, curved electrodes 14 and 16 deliver ions to two planar DMS analyzers 10. All configurations as will be contemplated by those of skill in the art in view of the disclosure are within the scope of the disclosure.

Figure 3:
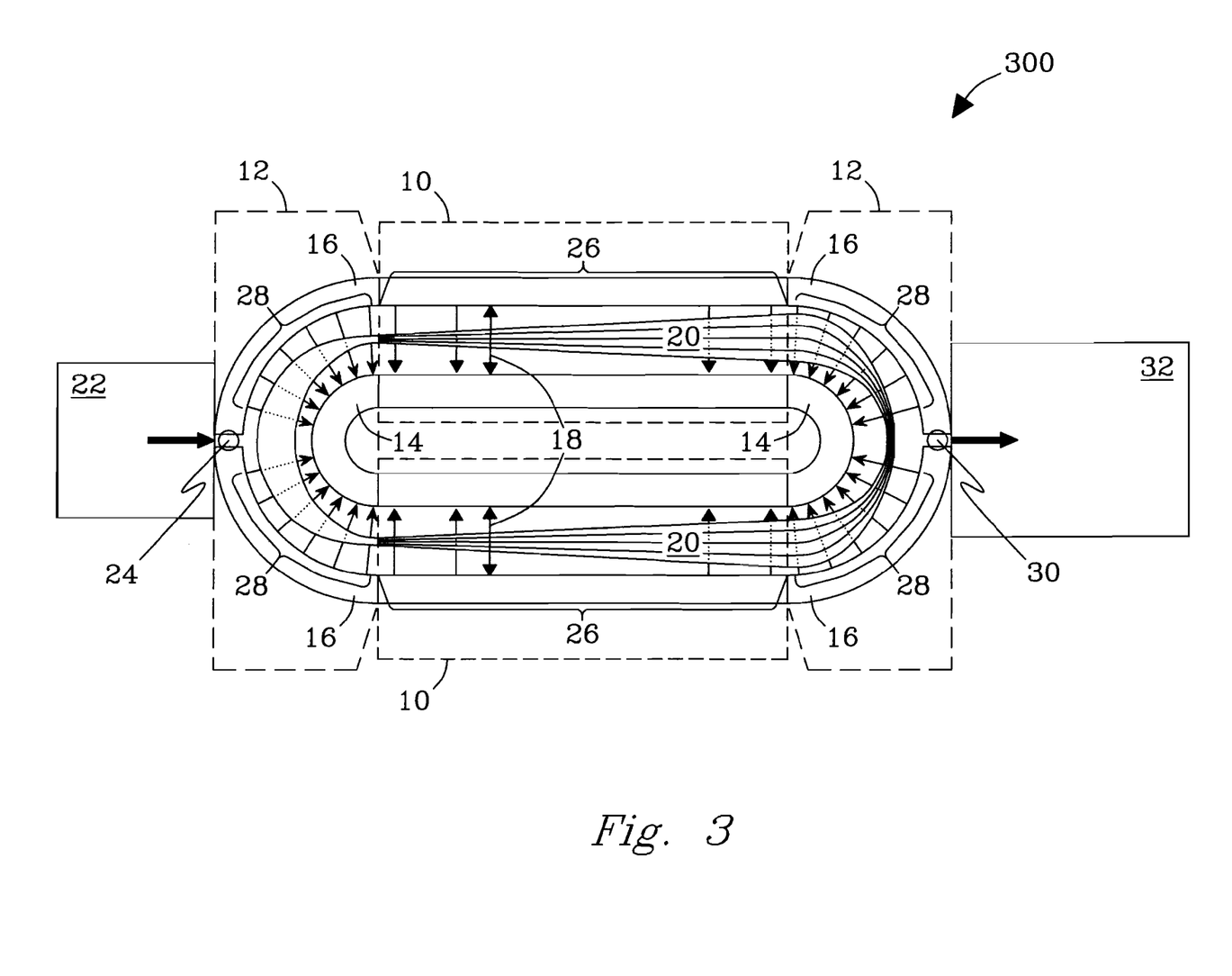
FIG. 3 is a cross-sectional view of a "hooked" DMS apparatus, according to yet another embodiment of the invention.

FIG. 3 illustrates a cross-section of a "hooked" DMS apparatus 300, according to yet another embodiment of the invention. In the instant embodiment, two planar DMS analyzers 10 are each coupled to, or integrated with, two DMS elements 12 each comprising two curved electrodes 14 and 16 with a gap 18 therebetween that receives ion beam 20 from either ion source or preceding stage 22 via aperture 24 or from a planar DMS analyzer 10. The first "hooked" DMS element 12 with angular span of 180° is coupled to ion source 22 and integrated with the ends of both planar DMS analyzers 10. The second "hooked" DMS element 12 with the same angular span is integrated with the other ends of both planar DMS analyzers 10 and positioned in front of subsequent stage 32, e.g., an IMS or MS. Curved electrodes 14 and 16 of first element 12 split ion beam 20 introduced from ion source or preceding stage 22 between two analyzers 10, each filtering ions received using a uniform electric field 26. Electrodes 14 in each element 12 carry $U_D(t)$ and electrodes 16 carry the CV that jointly establish a spatially inhomogeneous electric field 28 over gap 18 that focuses ion beam 20 introduced thereto toward the gap median. Thus, beam 20 is compressed, becoming thinner compared to diffuse beam 20 received from preceding stage 22 for first element 12 or either DMS analyzer 10 for second element 12. Ion beam 20 entering apparatus 300 is more effectively injected into DMS analyzers 10 and the beam exiting apparatus 300 is more effectively transmitted via aperture 30 to subsequent stage 32. In the instant embodiment, each stage 12 provides an angular turn of about 90° as measured from the drift vector in DMS analyzer 10 to which each element 12 is coupled, but is not limited. Other instrument configurations are envisioned, e.g., with ions injected into and/or ejected from the elements 12 at other than their midpoints. No limitations are thus intended.

Figure 4:
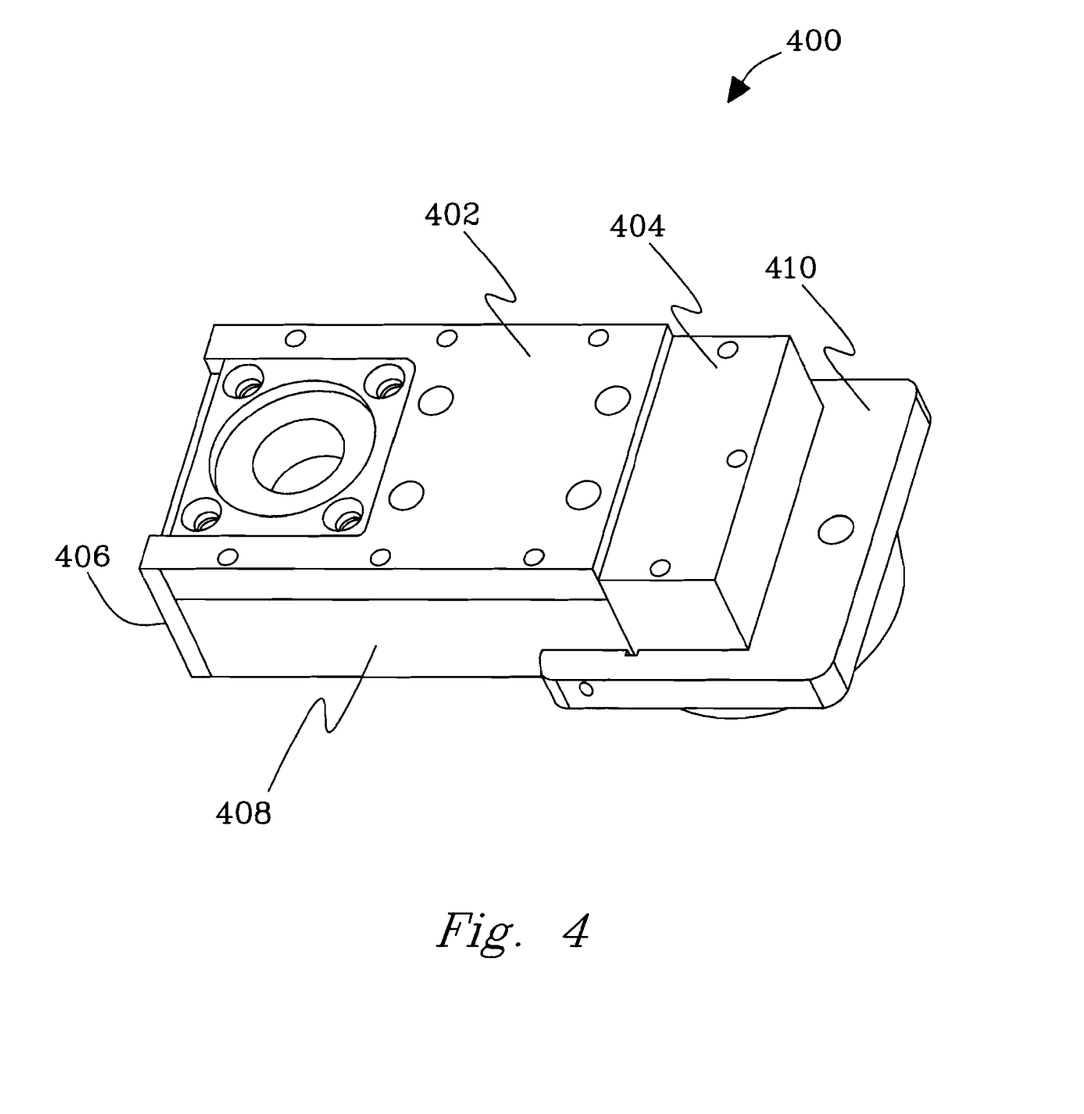
FIG. 4 shows a perspective view of an outer casing for enclosing an embodiment of a "hooked" DMS apparatus of the invention.

FIG. 4 presents a perspective view of an outer casing or enclosure 400 for enclosing an embodiment of a "hooked" DMS apparatus (FIG. 1) of the invention. Casing 400 includes a top part 402, a lid 404, a side panel 406, a bottom part 408, and an adaptor 410 machined out of a vacuum-compatible plastic, e.g., commercial Polyetheretherketone (PEEK®) (McMaster-Carr, Los Angeles, Calif., USA). In the exemplary embodiment, the planar DMS analyzer is formed by planar parts of two polished stainless steel electrodes precisely positioned inside enclosure 400 by ceramic spacers (not shown). Gap dimensions are 2 mm (width), 30 mm (length), and 20 mm (span). Ions are focused in a 2-mm annular gap between the cylindrical parts of two electrodes, with an inner radius of 8 mm and an outer radius of 10 mm.

Figure 5:
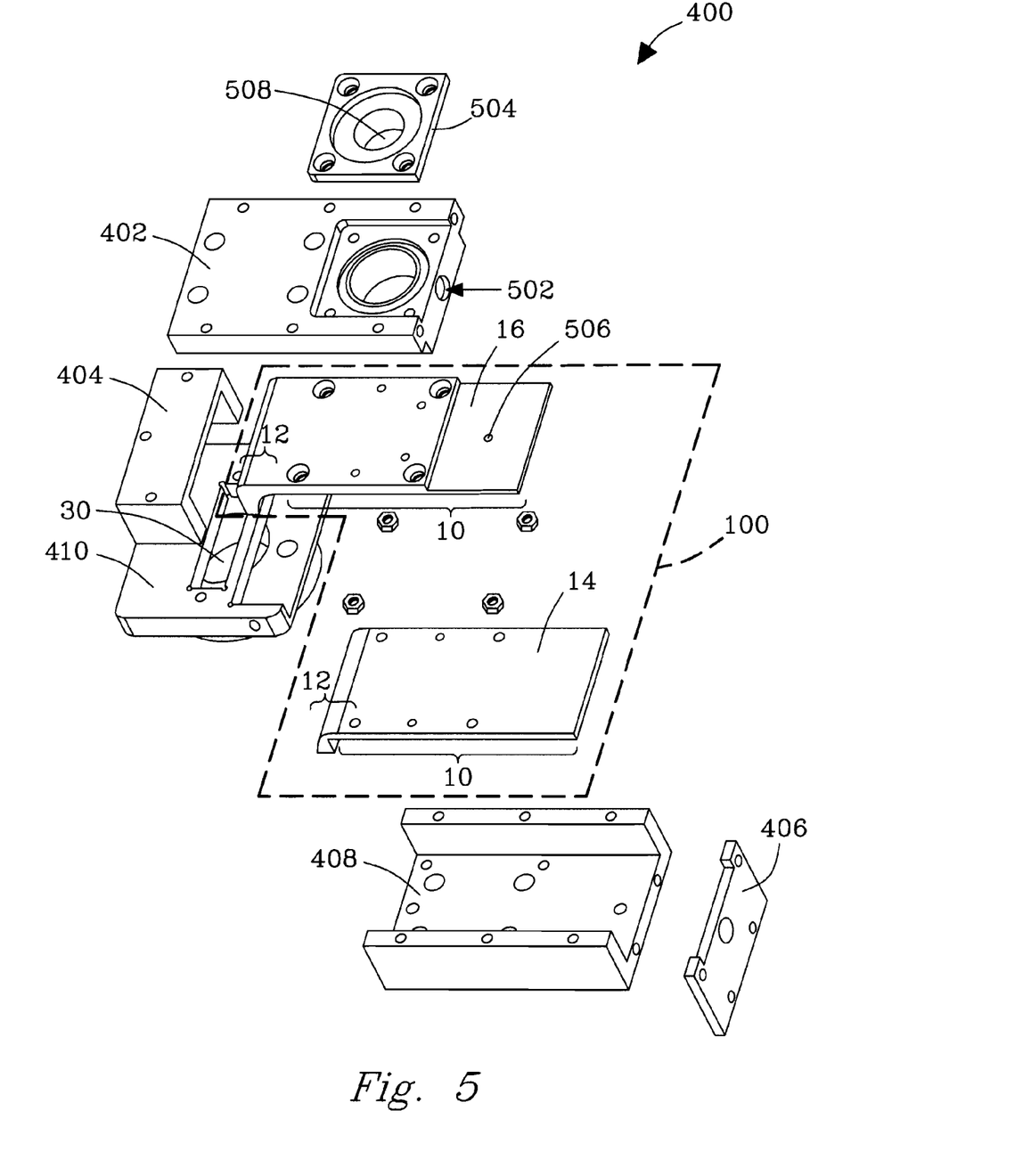
FIG. 5 presents an exploded view of the outer casing of FIG. 4 for enclosing a preferred embodiment of a "hooked" DMS apparatus of the invention.

FIG. 5 presents an exploded view of outer casing 400 of FIG. 4 showing parts of the exemplary embodiment of a "hooked" DMS apparatus 100 enclosed therein. Electrodes 14 and 16, described in reference to FIG. 1, comprise planar segments forming an analyzer 10 and cylindrical segments forming element 12 integrated into contiguous structures, but are not limited thereto. For example, planar and curved segments may be fabricated separately and joined by bolting, fastening, welding, soldering, gluing, and other methods without limitation. Electrodes 14 and 16 are positioned in parallel with a defined gap therebetween (FIG. 6) enclosed within casing 400. A gas inlet 502 in top part 402 introduces carrier gas into the gap found beneath curtain plate 504 through aperture 508 in curtain plate 504 and aperture 506 in electrode 16. Plate 504 is seated in, and secured to, top part 402. Adaptor 410 attaches apparatus 100 to inlet 30 of subsequent stage 32.

Figure 6:
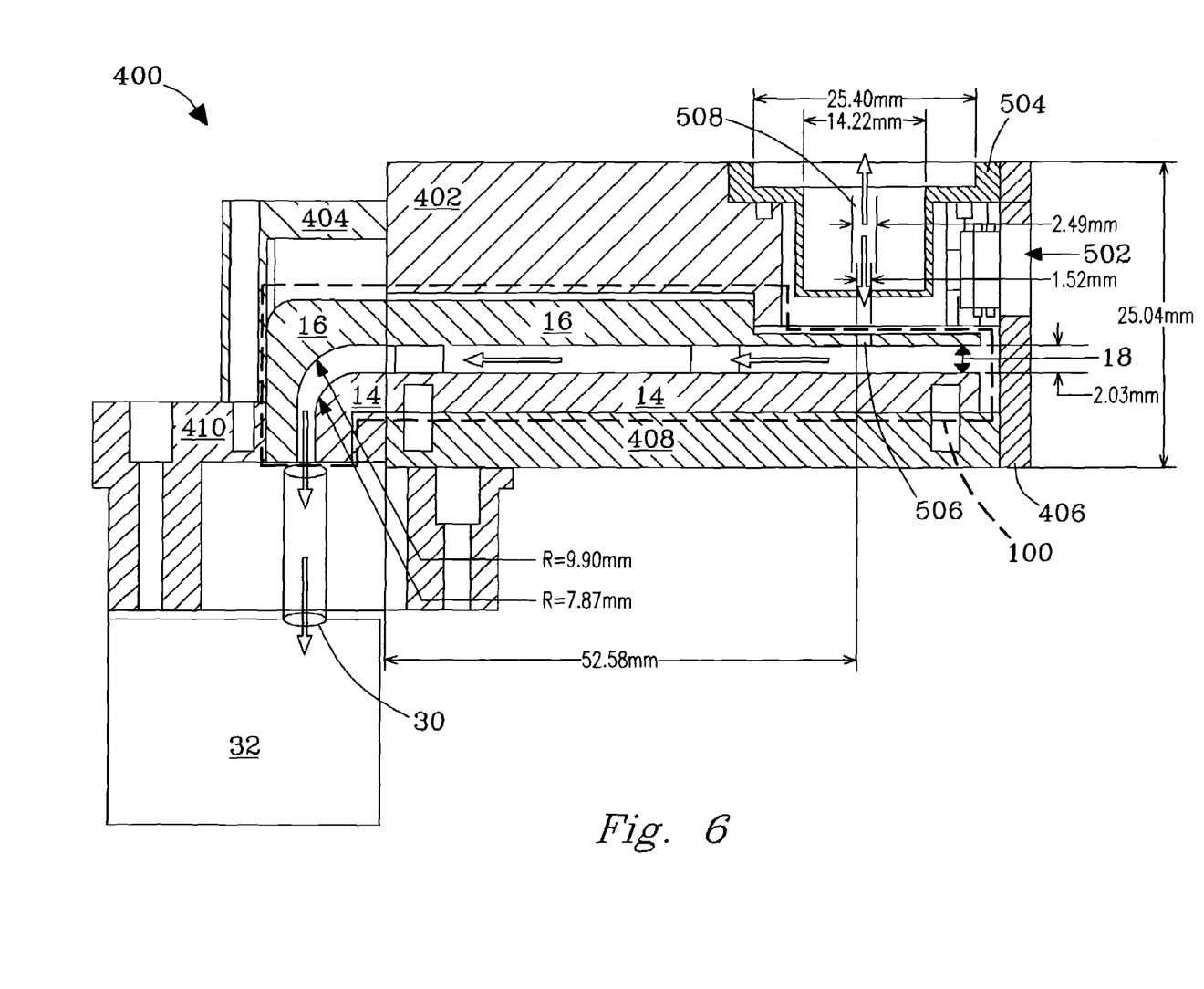
FIG. 6 is a cross-sectional view of a preferred embodiment of a "hooked" DMS apparatus integrated within an outer casing of FIG. 4.

FIG. 6 presents a cross-sectional view of the exemplary embodiment of a "hooked" DMS apparatus 100 assembled within the casing 400 of FIG. 4 described previously, including dimensions. Gas inlet 502 allows introduction of a suitable gas as will be known by those of skill in the art, including, e.g., $N_2$, He, $O_2$, $CO_2$, $SF_6$ and the like or mixtures thereof, providing: 1) a curtain gas to curtain plate 504 for desolvation of ions introduced thereto from an ion source (FIG. 1), e.g., an ESI emitter, and 2) a carrier gas to gap 18 between electrodes 14 and 16.

Figure 7:
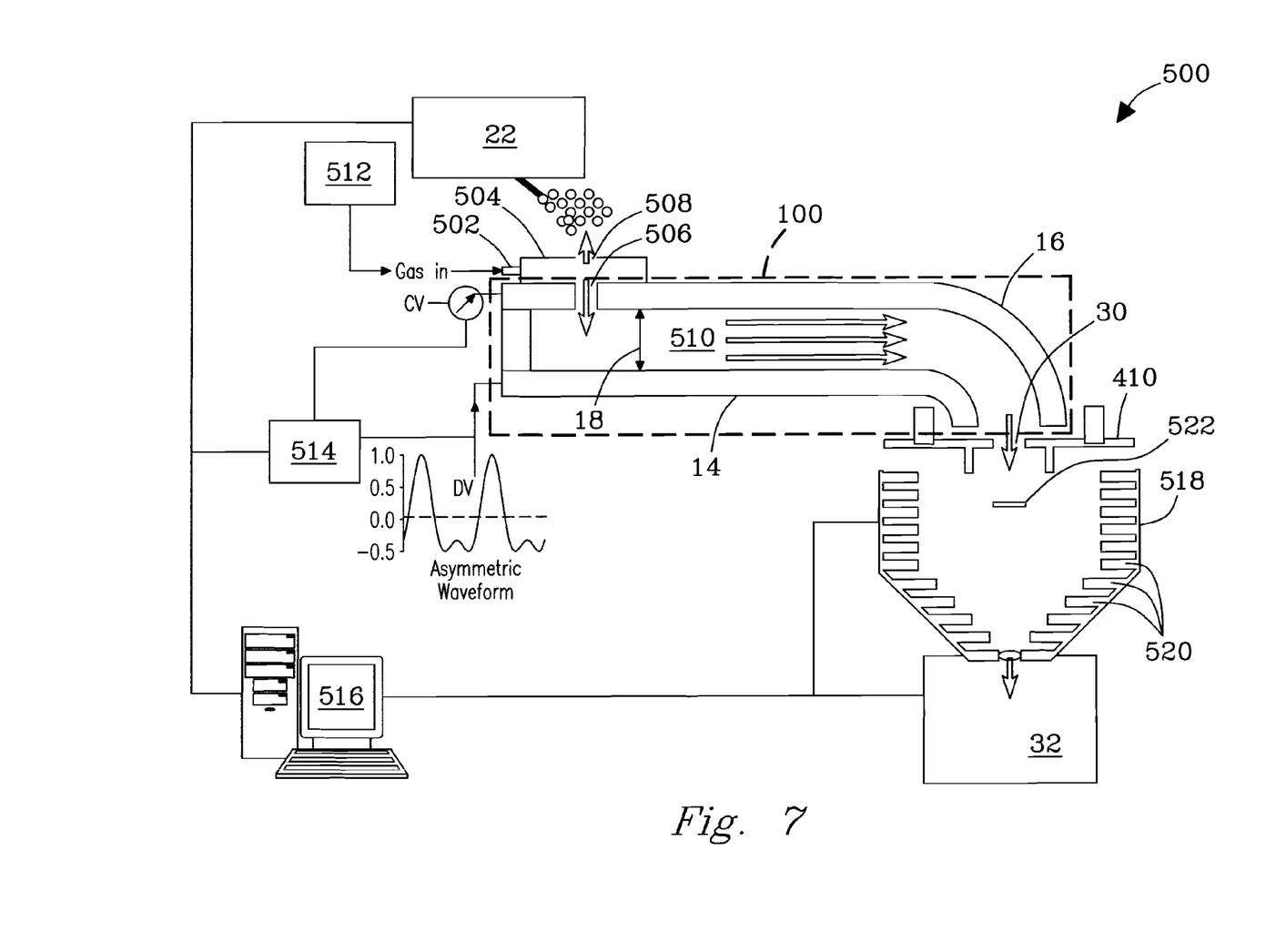
FIG. 7 illustrates an exemplary instrument configuration employing a preferred embodiment of a "hooked" DMS apparatus of the invention.

FIG. 7 illustrates an exemplary integrated DMS/MS instrument 500 involving a "hooked" DMS apparatus 100 of the invention and TOF MS stage 32. The person of skill in the art will understand that the configuration is illustrative, not exclusive. Thus, no limitations are intended. In the figure, apparatus 100 is coupled to ion source 22, here an ESI emitter. Ions enter gap 18 through curtain plate 504 or other suitable ESI/DMS interface. In the instant configuration, curtain plate aperture 508 and ion sampling aperture 506 have diameters of 2.5 mm and 1.5 mm, respectively. Carrier gas 510 enters through a gas inlet 502 or side opening in the top part of the casing (FIG. 5) and splits into two streams. A major stream flows out of curtain plate aperture 508 and desolvates ions incoming from ion source 22, while a minor stream carries ions into sampling aperture 506 and through gap 18. The exit from gap 18 opposes aperture 30, with a ~0.5 mm break left for electrical insulation and escape of excess carrier gas 510. Gas is supplied by a gas sourcing unit 512 (Thermo-Fischer Scientific, Waltham, Mass., USA) that formulates gas mixtures of up to three components each pre-dried by hygroscopic filters and controls the flow rate in the 0.5-5 L/min range. For example, $He/N_2$ mixtures can be supplied with compositions of 10% to 80% He (v/v) at total flow rates of ~1.5-4 L/min, but is not limited thereto. ESI emitter 22, mounted on an X-Y translation stage for fine position adjustment, is installed a few mm away from curtain plate aperture 508. Samples are infused to emitter 22 at a typical flow rate of 0.4 µL/min through a metal union, e.g., using a pump-driven microsyringe (KD Scientific, Holliston, Mass., USA). The CV is generated by a programmable dc power supply (Thermo-Fischer) 514, with waveform applied to electrode 14 and CV applied to electrode 16. The DV is adjustable from 2.3 kV to 4 kV. In the exemplary case, a DV=3.9 kV is used, but is not limited. In the instant case, DMS apparatus 100 is biased at 190 V, curtain plate 504 is at 1 kV, and ESI emitter 22 is at ~3 kV (referenced to ground). The FAIMS spectrum is obtained by scanning the desired CV range, with scan speed variable from about 0.5 V/s to about 5 V/s. All instrumental parameters are controlled by custom software resident on a dedicated PC 516. In the instant embodiment, MS analyzer 32 is an LC/MSD TOF instrument (Agilent Technologies, Palo Alto, Calif., USA) equipped with an ion funnel 518 (e.g., as detailed in U.S. Pat. Nos. 6,979,816, 6,818,890, and 6,967, 325 incorporated herein) instead of the standard capillary-skimmer cone interface, which significantly raises ion utilization efficiency at the atmospheric pressure ionization (API)/MS interface. Funnel 518 comprises ~100 circular electrodes 520 with IDs reducing from 25 mm at the "mouth" to 2 mm at the exit to MS 32, but is not limited thereto, and a standard jet disrupter 522 that improves sensitivity. Funnel 518 is evacuated by the original mechanical pump of TOF 32 and connected to the skimmer chamber. The capillary inlet normally leading into funnel 518 is replaced by an aperture cut through a 0.2 mm steel sheet. Three apertures are exemplary: 1) a circle of 0.43 mm diameter, 2) a non-contiguous "slit" made of 11 circular 0.13-mm holes disposed uniformly along a 4-mm segment, and 3) a similar slit with 0.19 mm holes. The cross-sectional area of apertures 1) and 2) is 0.145 mm$^2$, resulting in equal funnel pressure of 2 Torr, and that of aperture 3) is twice greater at 0.29 mm$^2$, resulting in proportionately larger pressure of 4 Torr. The rationale for a slit aperture is to maximize overlap with a ribbon-like ion beam exiting the hooked DMS apparatus 100. Funnel 518 focuses and guides broad or divergent ion beams in a pseudopotential well created by a combination of dc and rf voltages applied to electrodes 520. In the instant application, voltages are 187 V to 40 V dc along the funnel 518, 190 V on the aperture 30, and 175 V on jet disrupter 522. The peak rf amplitude is 45 V (at 560 kHz). All listed voltages are for positive ions, and would be reversed for negative ion analyses.

EXAMPLE

To test the capability of the invention to enhance transmission of ions filtered by planar FAIMS to following stages, common MS standards were analyzed using a planar FAIMS/TOF MS system. The instrument was configured with or without the FAIMS/MS interface of the invention described above in reference to FIG. 7, including a non-contiguous "slit" aperture made of 11 circular holes 0.19 mm in diameter, all other conditions being equal. This integrated configuration is exemplary of many like systems and is intended to be illustrative, not exclusive. All such systems as will be contemplated by those of skill in the art in view of the disclosure are within the scope of the invention. No limitations are intended.

Experimental. Solutions of reserpine (5 µM and 50 µM) and bradykinin (10 µM) in 50:49:1 methanol:water:acetic acid were used. The DMS unit described hereinabove was operated using a DV voltage of 3.9 kV and a CV scan rate of 5 V/min. Ion signals measured at the MS detector with a hooked DMS and a standard planar DMS for these samples are compared in FIGS. 8a-8c.

Figure 8A:
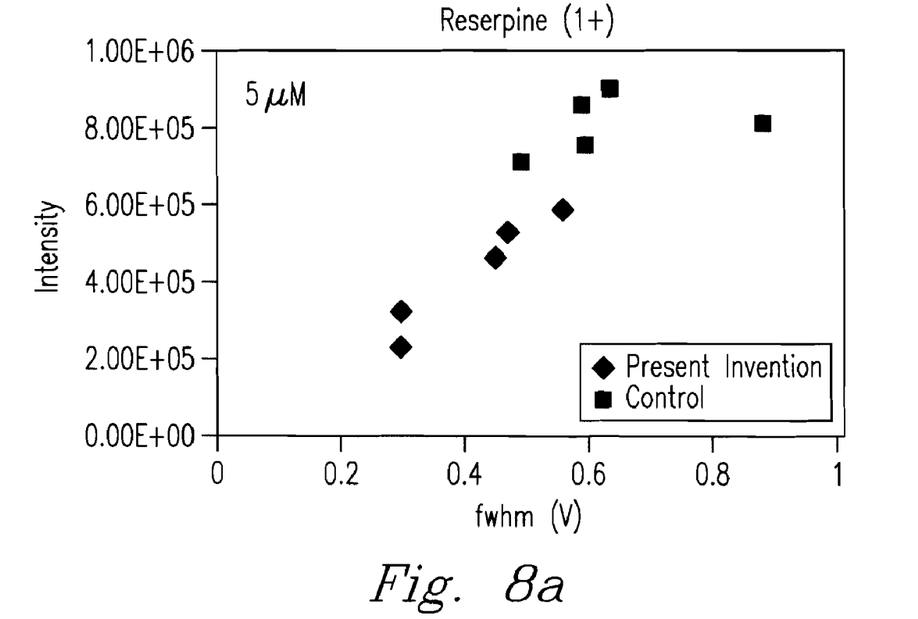
FIGS. 8a-8c present resolution-sensitivity diagrams for reserpine and bradykinin solutions analyzed using a planar DMS/time-of-flight mass spectrometry system with and without the DMS/MS interface of the invention.
Figure 8B:
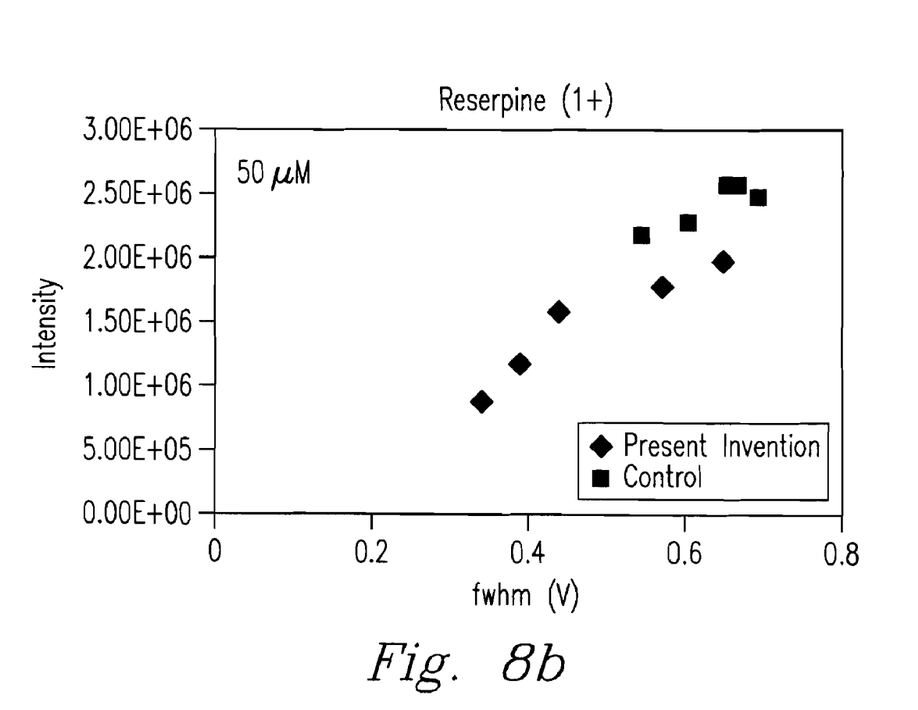
Figure 8C:
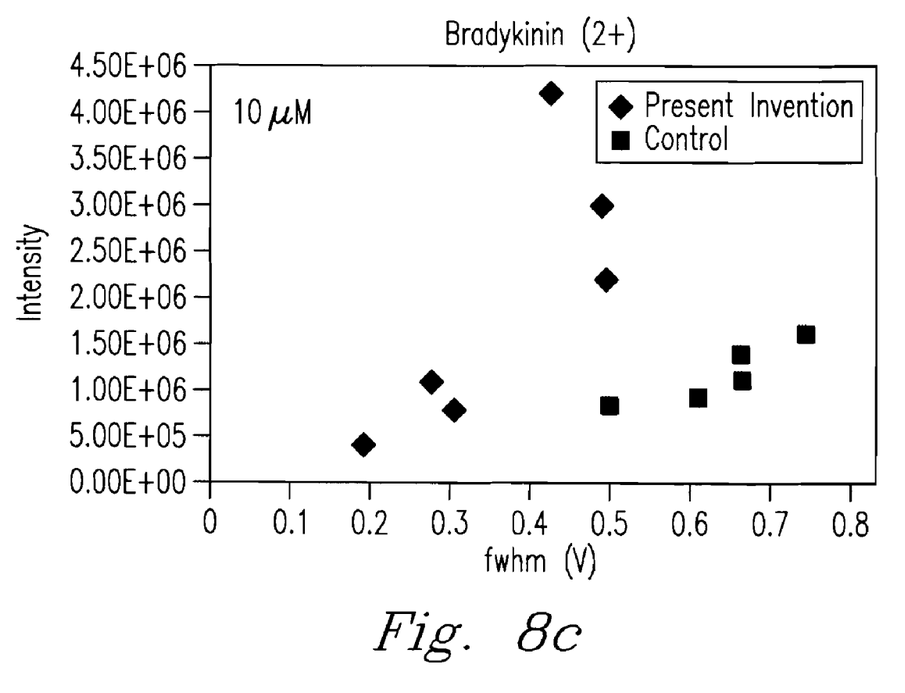

Results. The hooked DMS has improved sensitivity for bradykinin (2+) ions (FIG. 8c), but not for reserpine (1+) ions from either solution (FIGS. 8a and 8b). The difference is primarily due to ion focusing in the hooked DMS getting stronger at higher absolute CV values (here ~8 V for bradykinin and ~3 V for reserpine). As is well-known in the art, for peptide ions, higher absolute CVs are strongly correlated with higher charge states. Thus ion focusing in the hooked DMS preferentially raises the intensity of multiply-charged peptides, which may actually be welcome in proteomic analyses where relative suppression of (1+) ions that contain most chemical noise is often sought.

We claim:

1. An apparatus for improved interfacing of at least one differential mobility spectrometry (DMS) analyzer having substantially planar electrodes to other stages, comprising:
   at least two curved electrodes with a gap therebetween filled with a gas and operable for receiving ions introduced thereto, carrying a periodic asymmetric waveform and a dc compensation voltage that jointly establish spatially inhomogeneous electric field in said gap, which focuses said ions toward the median of said gap before and/or after said at least one DMS analyzer; and
   wherein the range of DMS separation parameters selected substantially includes that set by operation of said DMS analyzer such that said ions are focused to said gap median without significant losses, creating a thinner ion beam that is more completely transmitted through apertures of limited size to said other stages and/or more effectively injected into said DMS analyzer.

2. An apparatus of claim 1, operably coupled to an ionization source selected from the group consisting of electrospray (ESI), thermospray, sonic spray, desorption ESI (DESI), matrix assisted laser desorption ionization (MALDI) and atmospheric pressure MALDI (AP-MALDI), surface-enhanced laser desorption ionization, chemical ionization (CI) and atmospheric pressure CI (APCI), photoionization and atmospheric pressure photoionization, laser vaporization or desorption, secondary ion ionization, arc discharge, inductively coupled plasma, coronary or cathode discharge, electron impact, liquid evaporation, liquid clustering, "pick-up", and combinations thereof.

3. An apparatus of claim 1, wherein said DMS analyzer operates on the principles of field asymmetric waveform ion mobility spectrometry (FAIMS).

4. An apparatus of claim 1, wherein said DMS analyzer operates on the principles of higher-order differential ion mobility spectrometry (HODIMS).

5. An apparatus of claim 1, wherein said DMS analyzer operates on the principles of ion-mobility spectrometry with alignment of the dipole direction (IMS-ADD).

6. An apparatus of claim 1, wherein ions are driven through said gap between said curved electrodes by flow of said gas.

7. An apparatus of claim 6, wherein said gas is selected from the group consisting of $H_2$, He, $N_2$, $O_2$, $CO_2$, $SF_6$, and mixtures thereof.

8. An apparatus of claim 7, wherein said gas is a mixture comprising He at a concentration in the range from about 10% to about 90% by volume.

9. An apparatus of claim 1, wherein ions are driven through said gap between said curved electrodes by a component of electric field directed along said gap.

10. An apparatus of claim 1, wherein one set of said curved electrodes receives ions from at least two different DMS analyzers.

11. An apparatus of claim 1, wherein one set of said curved electrodes delivers ions to at least two different DMS analyzers.

12. An apparatus of claim 1, comprising two sets of said curved electrodes, wherein one set delivers ions to said at least one substantially planar DMS analyzer and the other set receives ions from that analyzer.

13. An apparatus of claim 12, wherein the number of said DMS analyzers is two.

14. An apparatus of claim 1, wherein the gap width between said curved electrodes substantially equals the distance between said DMS analyzer electrodes and said waveform applied to said curved electrodes substantially matches that used in said DMS analyzer.

15. An apparatus of claim 1, wherein at least one of said curved electrodes is contiguous with at least one of said DMS analyzer electrodes.

16. An apparatus of claim 15, wherein one of said curved electrodes is contiguous with one of said DMS analyzer electrodes and the other of said curved electrodes is contiguous with the other of said DMS analyzer electrodes, such that the same waveform is loaded simultaneously on said curved electrodes and said DMS analyzer electrodes coupled thereto.

17. An apparatus of claim 1, wherein said curved electrodes are cylindrical segments produced by resection of an angular arc from two coaxial cylinders and positioned such that the cylindrical axis is parallel to the plane of said DMS analyzer and the annular gap median is substantially coincident with the median of the gap of said DMS analyzer at the point of closest proximity between said curved electrodes and said DMS analyzer electrodes.

18. An apparatus of claim 17, wherein the span of said angular arc is between 0 degrees and about 270 degrees.

19. An apparatus of claim 17, wherein the span of said angular arc is between about 30 and about 180 degrees.

20. An apparatus of claim 17, wherein the span of said angular arc is about 90°.

21. An apparatus of claim 17, wherein the radius of said annular gap median is between about 1 mm and about 100 mm.

22. An apparatus of claim 17, wherein the radius of said annular gap median is between about 3 mm and about 30 mm.

23. An apparatus of claim 1, wherein the gap width between said curved electrodes is between about 0.2 mm and about 10 mm.

24. An apparatus of claim 1, wherein the gap width between said curved electrodes is between about 0.4 mm and 5 mm.

25. A method for improved interfacing of a differential mobility spectrometry (DMS) analyzer having substantially planar electrodes to other stages, comprising the steps:
providing at least two curved electrodes with a gap therebetween filled with a gas, carrying a periodic asymmetric waveform and a dc compensation voltage that jointly establish spatially inhomogeneous electric field in said gap that focuses ions before and/or after said DMS stage toward the median of said gap; and
wherein the range of DMS separation parameters selected substantially includes that set by operation of said DMS analyzer such that ions are focused to said gap median without significant losses, creating a thinner ion beam more completely transmitted through apertures of limited size leading to said other stages and/or more effectively injected into said DMS analyzer.

26. A method of claim 25, wherein said DMS analyzer operates on the principles of field asymmetric waveform ion mobility spectrometry (FAIMS).

27. A method of claim 25, wherein said DMS analyzer operates on the principles of higher-order differential ion mobility spectrometry (HODIMS).

28. A method of claim 25, wherein ions are driven through said gap between said curved electrodes by flow of said gas.

29. A method of claim 25, wherein ions are driven through said gap between said curved electrodes by a component of electric field directed along said gap.

30. A method of claim 25, wherein one set of said curved electrodes receives ions from at least two different DMS analyzers.

31. A method of claim 25, wherein one set of said curved electrodes delivers ions to at least two different DMS analyzers.

32. A method of claim 25, wherein one set of said curved electrodes delivers ions to said at least one DMS analyzer and another set of said curved electrodes receives ions from that analyzer.

33. A method of claim 25, wherein the gap width between said curved electrodes substantially equals the distance between said DMS analyzer electrodes and said waveform applied to said curved electrodes substantially matches that used in said DMS analyzer.

34. A method of claim 25, wherein at least one of the said curved electrodes is contiguous with at least one of said DMS analyzer electrodes.

35. A method of claim 34, wherein one of the said curved electrodes is contiguous with one of the said DMS analyzer electrodes and the other of the said curved electrodes is contiguous with the other of the said DMS analyzer electrodes, such that the same waveform is loaded simultaneously on said curved electrodes and said DMS analyzer electrodes coupled thereto.

36. A method of claim 25, wherein said curved electrodes are cylindrical segments produced by resection of an angular arc from two coaxial cylinders and positioned such that the cylindrical axis is parallel to the plane of said DMS analyzer and the annular gap median is substantially coincident with the median of the gap of said DMS analyzer at the point of closest proximity between said curved electrodes and said DMS analyzer electrodes.

37. A method of claim 36, wherein the span of said angular arc is between 0 degrees and about 270 degrees.

38. A method of claim 36, wherein the span of said angular arc is between about 30 degrees and about 180 degrees.

39. A method of claim 36, wherein the span of said angular arc is about 90°.

40. A method of claim 36, wherein the radius of said annular gap median is between about 1 mm and about 100 mm.

41. A method of claim 36, wherein the radius of said annular gap median is between about 3 mm and about 30 mm.

42. A method of claim 25, wherein the gap width between said curved electrodes is between about 0.2 mm and about 10 mm.

43. A method of claim 25, wherein the gap width between said curved electrodes is between about 0.4 mm and about 5 mm.

* * * * *

UNITED STATES PATENT AND TRADEMARK OFFICE
CERTIFICATE OF CORRECTION

PATENT NO. : 7,491,930 B2  Page 1 of 1
APPLICATION NO. : 11/617889
DATED : February 17, 2009
INVENTOR(S) : A A Shvartsburg et al.

It is certified that error appears in the above-identified patent and that said Letters Patent is hereby corrected as shown below:

Correct Column 1, lines 5 through 8 of the issued patent as follows:

The invention was made with Government support under grant number RR018522 from the U.S. National Institutes of Health and contract DE-AC05-76RL01830 awarded by the US Department of Energy. The government has certain rights in the invention.

Signed and Sealed this
Eleventh Day of September, 2012

David J. Kappos
*Director of the United States Patent and Trademark Office*